United States Patent [19]

Helling et al.

[11] Patent Number: 5,057,276
[45] Date of Patent: Oct. 15, 1991

[54] PROCESS FOR THE PREPARATION OF REAGENT LAYERS CONTAINING HYDROPHOBIC REAGENTS

[75] Inventors: Günter Helling, Odenthal; Wolfgang Himmelmann, Leverkusen, both of Fed. Rep. of Germany; Gary Oosta, Elkhart, Ind.; Helmut Reiff, Leverkusen, Fed. Rep. of Germany; Alexander Riebel, Leverkusen, Fed. Rep. of Germany; Karl Schranz, Odenthal-Hahnenberg, Fed. Rep. of Germany

[73] Assignee: Miles Inc., Elkhart, Ind.

[21] Appl. No.: 52,998

[22] Filed: May 22, 1987

[30] Foreign Application Priority Data

May 28, 1986 [DE] Fed. Rep. of Germany ....... 3618049

[51] Int. Cl.$^5$ ............................................. G01N 21/78
[52] U.S. Cl. ..................................... 422/56; 252/312; 252/314; 252/408.1; 436/169; 436/170; 427/2

[58] Field of Search ....................................... 436/8–18, 436/169, 170; 252/408.1, 312, 314; 435/12, 19; 422/56; 427/2

[56] References Cited

U.S. PATENT DOCUMENTS 3,997,470 12/1976 Monte et al. ........................ 436/14
4,343,897 8/1982 Neumann et al. .................... 436/17

Primary Examiner—Robert J. Hill, Jr.
Attorney, Agent, or Firm—Roger N. Coe

[57] ABSTRACT

Process for the preparation of stable dispersions of hydrophobic reagents in aqueous material, which process involves dissolving an ionomeric polymer, together with hydrophobic reagent substance, in a suitable organic solvent, adding water to the resulting material and then removing the organic solvent. The resulting dispersion has exceptionally high stability and finds utility in the production of diagnostic reagent test devices.

8 Claims, No Drawings

PROCESS FOR THE PREPARATION OF REAGENT LAYERS CONTAINING HYDROPHOBIC REAGENTS

FIELD OF THE INVENTION

The present invention relates to a process for the preparation of stable dispersions of hydrophobic reagents in water or aqueous systems using ionomeric polymers as carriers and to the use of these dispersions in the production of test strips. The dispersions are prepared by dissolving the ionomeric polymer, together with the hydrophobic substance (reagent), in a suitable organic solvent, adding water to this solution and then removing the organic solvent. The dispersion thus obtained has an exceptionally high stability and can very readily be used in the production of test strips.

BACKGROUND OF THE INVENTION

Clinical chemistry investigations with biological fluids have been substantially simplified in recent years by the development of the so-called "dry chemistry". Thus, for example, the development of test strips or devices for determination of glucose in whole blood provided the possibility of diabetics carrying out a check on their blood sugar level by themselves. Indeed, this check has already become an important component of the therapy of diabetics. Moreover, the use of test strips is not limited only to the determination of glucose. Test strips for enzymatic determinations, substrates, such as, for example, cholesterol or triglycerides, or ions or for drug monitoring are not well known.

Many examples of so-called "dry chemical" determination systems, also called test strips, are described in the literature. The reagents necessary for such test strips normally are contained in a carrier matrix. The sample containing the analysis substance is applied to the test strip. The sample material, blood, serum, urine or another biological fluid, can be applied diluted or undiluted. A reaction which generates a detectable signal (for example coloration or fluorescence) which is proportional to the concentration of the analysis substance then takes place in the test strip.

Many materials are known to be suitable as the carrier matrix, such as, for example, paper, plastics, gelatin or cellulose derivatives.

In the production of test strips, it is frequently necessary for hydrophobic substances also to be introduced into the carrier matrix.

It is known that one possibility for introducing hydrophobic substances into the carrier matrix is by impregnation of the matrix with an organic solution of the substances. In this type of production, however, two or even more impregnating and drying steps are usually necessary, since hydrophilic substances which are soluble in aqueous systems frequently also have to be introduced into the matrix. Another possibility is to prepare emulsions of the substances. This requires a large amount of energy, however, to achieve a sufficiently fine distribution of the substances.

Surprisingly, it has now been found that aqueous dispersions of hydrophobic reagents can be prepared by a very simple process using ionomeric polymers. These dispersions have an excellent stability and small particle size. They can, therefore, be very readily used in the preparation of reagent layers.

DESCRIPTION OF PREFERRED EMBODIMENTS

The preparation of dispersions of hydrophobic reagents in water by charging an ionically modified polymer with the hydrophobic reagent is characterized in that the hydrophobic reagent, together with an ionomeric polyaddition or polycondensation product, is dissolved in an organic water-miscible solvent with a boiling point of less than 120° C. or in a mixture of organic solvent with water in a weight ratio of 50:50 to 100:0, preferably 75:25 to 95:5, water is added to the solution, so that a solvent/water mixture in a weight ratio of 10:1 to 1:10 is present, and the organic solvent is then removed.

The ionomeric polyaddition or polycondensation products according to the invention contain 4 to 180 milliequivalents of ionic groups or groups which can be converted into ionic groups per 100 grams (g) and/or 1 to 20% by weight of alkylene oxide units of the formula —$CH_2$—$CH_2$—O— incorporated within a polyether chain, it being possible for the products to contain the polyether chain in a lateral position or in the main chain. Ionomeric polyaddition or polycondensation products containing 10 to 50 milliequivalents of ionic groups or groups which can be converted into ionic groups are particularly preferred.

The ionomeric polyaddition or polycondensation products, referred to as "ionomeric products" herein, which can be used according to the invention include polyurethanes, polyesters, polyamides, polyureas, polycarbonates, polyacetals and polyethers. Other ionomeric products which simultaneously belong to two or more types of polymer, such as, for example, polyester-polyurethanes, polyether-polyurethanes and polyester-ureas which contain 4 to 100 and preferably 10 to 50 milliequivalents of ionic groups per 100 g and/or 1 to 20% by weight of ethylene oxide units of the formula —$CH_2$—$CH_2$—O— incorporated within a polyethylene chain, it being possible for the products to contain the polyether chain in the lateral position or in the main chain. Especially preferred ionomeric products are polyurethanes.

Ionomeric products, such as are used according to the invention, are known as such and are described, for example, in *Angewandte makromolekulare Chemie*, 26 (1972), pages 85–106; *Angewandte Chemie*, 82 (1970), pages 53 et seq.; *J. Oil. Col. Chem. Assoc.*, 53 (1970), page 363. Other descriptions of suitable ionomeric products are to be found in DE-OS (German Published Specifications) 2,642,973; 2,651,505; 2,651,506; 2,659,617; 2,729,245; 2,730,514; 2,732,131; 2,734,576 and 2,811,148.

Ionomeric products with anionic groups are preferred. Ionomeric products which are particularly suitable for the process of the invention are described in German Patent Specification 1,472,746. These ionomeric products are based on polyurethanes which are obtained from compounds with several reactive hydrogen atoms with a molecular weight of 300 to 10,000, polyisocyanates and, if appropriate, chain-lengthening agents with reactive hydrogen atoms. During the preparation of these polyurethanes or thereafter, isocyanate groups still present are reacted with a compound having at least one active hydrogen atom and at least one salt-like group or group which is capable of salt formation. If compounds with groups which are capable of salt formation are used, the resulting anionic polyurethanes are then converted at least partly into the salt form in a known manner.

The following groups are to be understood under the expression "salt-like groups":

—SO$_3^-$ and —COO$^-$;

4 to 180 milliequivalents of ionic groups or groups which can be converted into ionic groups being used per 100 g.

Examples of suitable starting components for the preparation of the anionic polyurethanes are described below:

I. Compounds With Active Hydrogen Atoms

These compounds are essentially linear and have a molecular weight of about 300 to 10,000, preferably 500 to 4,000. The compounds, which are known per se, have terminal hydroxyl and amino groups. Preferred polyhydroxy compounds are polyesters. The hydroxyl number of these compounds accordingly corresponds to about 370 to 10, in particular 225 to 28.

Examples of polyethers which may be mentioned are the polymerization products of ethylene oxide, propylene oxide, tetrahydrofuran and butylene oxide and their copolymerization or graft polymerization products, as well as the condensates obtained by condensation of polyhydric alcohols or mixtures thereof and the products obtained by alkoxylation of polyhydric alcohols.

Examples of possible polyacetals are the compounds which can be prepared from hexanediol and formaldehyde. Suitable polyesters, polyester-amides and polyamides are the predominantly linear condensates obtained from polybasic saturated carboxylic acids and polyfunctional saturated alcohols, amino-alcohols, diamines and mixtures thereof.

Polyhydroxy compounds which already contain urethane or urea groups and optionally modified natural polyols, such as castor oil or carbohydrates, can also be used.

Mixtures of various polyhydroxy compounds can, of course, be used for varying the lyophilicity or hydrophobicity and the mechanical properties of the process products.

II. Polyisocyanates

Suitable polyisocyanates are all the aromatic and aliphatic diisocyanates, such as, for example, 1, 5-naphtylene diisocyanate, 4, 4'-diphenylmethane diisocyanate, 4, 4'-diphenyldimethylmethane diisocyanate, di- and tetra-alkyldiphenylenemethane diisocyanate, 4, 4'-dibenzyl diisocyanate, 1, 3-phenylene diisocyanate, 1, 4-phenylene diisocyanate, the isomers of toluylene diisocyanate, optionally as a mixture, and preferably the aliphatic diisocyanates, butane 1, 4-diisocyanate, hexane 1, 6-diisocyanate, dicyclohexylmethane diisocyanate, cyclohexane, 1, 4-diisocyanate and isophorone diisocyanate.

III. Chain-Lengthening Agents

The chain-lengthening agents with reactive hydrogen atoms include:

1.) the customary glycols, such as ethylene glycol or condensates of ethylene glycol, butanediol, propane-1, 2-diol, propane -1, 3-diol, neopentylglycol, hexanediol, bis-hydroxymethylcyclohexane and dioxyethyldiane;

2.) the aliphatic, cycloaliphatic and aromatic diamines, such as ethylenediamine, hexamethylenediamine, 1, 4-cyclohexylenediamine, benzidine, diaminodiphenylmethane, the isomers of phenylenediamine, hydrazine and ammonia;

3.) amino-alcohols, such as ethanolamine, propanolamine and butanolamine; 4.) polyfunctional amines or hydroxy compounds, such as diethylenetriamine, triethylenetetramine, tetraethylenepentamine, pentaethylenehexamine, hexaethyleneheptamine, glycerol, erythtritol, 1, 3-diaminoisopropanol, 1, 2-diaminopropanol, and the monooxyalkylated polyamines, such as, for example, N-oxyethylenediamine, N-oxyethylhydrazine and N-oxyethylhexamethylenediamine; and 5.) water.

IV. Compounds Capable of Salt Formation

1.) Compounds with a ready-formed acid grouping.

a.) hydroxyacids, such as, for example, glyceric acid, lactic acid, trichlorolactic acid, malic acid, dihydroxymaleic acid, dihydroxyfumaric acid, tartaric acid, dihydroxytartaric acid, citric acid, dimethylolpropionic acid and dimethylolbutyric acid, the aliphatic, cycloaliphatic, aromatic and heterocylic mono- and diaminocarboxylic acids, such as glycine, $\alpha$- and $\beta$-alanine, 6-aminocaproic acid and 4-aminobutyric acid, the isomeric mono-and diaminobenzoic acids and the isomeric mono- and diaminonaphthoic acids;

b.) hydroxy- and carboxysulphonic acids; 2-hydroxyethane-sulphonic acid, phenol-2-sulphonic acid, phenol-3-sulphonic acid, phenol-4-sulphonic acids, phenol-2, 4-sulphonic acid, sulphoacetic acid, m-sulphobenzoic acid, p-sulphobenzoic acid, 1-benzoic acid-3, 5-disulphonic acid, 2-chloro-1-benzoic acid-4-sulphonic acid, 2-hydroxy-1-benzoic acid-5-sulphonic acid, 1-naphtholsulphonic acid, 1-naphtholdisulphonic acid, 8-chloro-1-naphtholdisulphonic acid, 1-naphtholtrisulphonic acids, 2(2)-naphthol-1-sulphonic acid and 2-naphtholtrisulphonic acid;

c.) aminosulphonic acids; amidosulphonic acid, hydroxylamine-monosulphonic acid, hydrazinedisulphonic acid, sulphanilic acid, N-phenylaminomethylsulphonic acid, 4, 6-dichloroaniline-2sulphonic acid, phenylene-1, 3-diamine-4, 6disulphonic acid, naphthylamine-1-sulphonic acid, naphtylamine-2-sulphonic acid, naphthylaminedisulphonic acid, naphtylamine-trisulphonic acid, 4, 4'-di-(p-aminobenoylamino)-diphenylurea-3, 3' disulphonic acid, phenylhydrazine-2, 5-disulphonic acid, taurine, methyltaurine, butyltaurine, 3-amino-l-benzoic acid-5-sulhponic acid, 3-amino -toluene-N-methane-sulphonic acid, 4,6-diamino -benzne-1,3-disulphonic acid, 2,4-diamino-5toluenesulphonic acid, 4, 4'-diamino-diphenyl-2, 2'disulphonic acid, 2-aminophenol-4-sulphonic acid, 4,4'-diamino-diphenylether-2-sulphonic acid, 2-aminoaminsole-N-methane-sulphonic acid, 2-amino -diphenylamine-sulphonic acid, ethylene glycol sulphonic acid, 2, 4-diaminobenzenesulphonic acid and N-sulphonato ethylethylenediamine; compounds which are especially preferred according to the invention are the alkali metal or ammonium salts of 2-aminoethyl-$\beta$-aminoethanesulphonic acid, of 2-aminoethyl-$\beta$-aminopropionic acid and of dimethylolpropionic acid, and the compound of the formula:

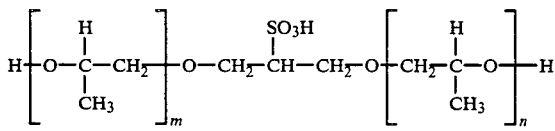

wherein: the sum of m and n is 2 to 6.

d.) the hydroxy- and aminocarboxylic acids and -sulphonic acids and polycarboxylic and -sulphonic acids furthermore include the (optionally hydrolyzed) addition products of unsaturated acids, such as acrylic acid, methacrylic acid, vinylsulphonic acid and styrenesulphonic acid, and unsaturated nitriles, such as acrylonitrile, of cyclic dicarboxylic acid anhydrides, such as maleic acid, phthalic acid and succinic anhydride, of sulphocarboxylic acid anhydrides, such as sulphoacetic and o-sulphobenzoic anhydride, of lactones, such as β-propiolactone and γ-butyrolactone, the addition products of the reaction products of olefins with sulphur trioxide, such as carbylsulphate, of epoxycarboxylic and -sulphonic acids, such as glycidic acid and 2, 3-epoxypropanesulphonic acid, of sultones, such as 1, 3-propanesultone, 1, 4-butanesultone and 1, 8-naphthylsultone, of cyclic sulphates, such as glycol sulphate, or of disulphonic acid anhydrides, such as benzene-1, 2-disulphonic acid anydride, onto aliphatic and aromatic amines, such as 1, 2-ethylenediamine, 1, 6-hexamethylenediamine, the isomeric phenylenediamines, diethylenetriamine, triethylenetetramine and tetraethylenepentamine and furthermore the addition products of sodium bisulphite onto olefinically unsaturated compounds, such as allyl alcohol, maleic acid and maleic acid bis-ethylene and bis-propylene glycol esters;

e.) hydroazinecarboxylic acids, such as hydrazinedicarboxylic acids.

Reactive compounds with 3 to 7 ring members which contain salt-like groups or groups which, after ring opening, are capable of salt formation:

a.) dicarboxylic acid anydrides, such as succinic anhydride, maleic anhydride and optionally hydrogenated phthalic anydride;

b.) tetracarboxylic acid dianhydrides, such as 1, 2, 4, 5-benzenetetracarboxylic acid anhydride;

c.) disulphonic acid anhydrides, such as benzene-1, 2-disulphonic acid anhydride;

d.) sulphocarboxylic acid anhydrides, such as sulphoacetic anydride and o-sulphobenzoic anhydride;

e.) sultones, such as 1, 3-propanesultone, 1, 4-butanesultone and 1, 8-naphthsultone;

f.) lactones, such as β-propiolactone and γ-butyrolactone;

g.) epoxycarboxylic acids, such as glycidic acid, if appropriate in the form of their alkali metal salts;

h.) epoxysulphonic acids, such as 2, 3-epoxy -propane-1-sulphonic acid, if appropriate in the form of their alkali metal salts, and the adducts of epoxyaldehydes and alkali metal bisulphites, such as, for example, the bisulphite compound of glycidylaldehyde.

The above acid groupings can be converted into the salt form in the customary manner by reaction with the compounds mentioned below: inorganic base, compounds which are basic or split off bases, such as monovalent metal hydroxides, carbonates and oxides, such as sodium hydroxide, potassium hydroxide, sodium carbonate, potassium carbonate and sodium bicarbonate. Furthermore, organic bases, such as tertiary amines, for example trimethylamine, triethylamine, dimethylaminoethanol and dimethylaminopropanol, ammonia and the like.

Suitable build-up components are furthermore, for example, mono- or dihydric alcohols which contain ethylene oxide units incorporated within polyether chains.

If such monofunctional nonionic hydrophilic polyethers are also used, it may frequently be of advantage to prevent premature chain stopping by also using build-up components which are more than difunctional. The monofunctional polyethers of the general formula last mentioned are prepared by processes which are known per se, such as are described, for example, in U.S. Pat. No. 3,905,929; 4,190,566 or 4,237,264.

Such build-up components impart additionally point-form hydrophilicity, electrolyte stability, stability on freezing and improved lubricating properties to the polyurethanes to be used according to the invention.

The amount of polyisocyanates is preferably chosen so that all the groups which are capable of reacting with isocyanate groups react.

If appropriate, the reaction is carried out by also using solvents, low-boiling solvents with a boiling point of less than 120° C., such as, for example, acetone, ethanol, methanol, tert-butanol, methyl ethyl ketone, acetonitrile, tetrahydrofuran and dioxane, which can optionally contain a proportion of water, preferably being suitable. Water, if appropriate without the addition of organic solvents, can be used as the solvent for inorganic bases and compounds with at least one hydrogen atom which reacts with isonate groups and at least one salt-like group or group capable of salt formation.

The predominantly linear high molecular weight anionic polyurethanes are in general obtained as clear to slightly opalescent solutions in the polar solvents mentioned. Their solids content is about 5 to 50% by weight of ionic polyurethane.

The preparation process for the ionomeric products used according to the invention may be illustrated by the following examples:

Polymer I

An NCO prepolymer (1.78% of NCO) is prepared from 800 g (0.356 mol) of a polyester of adipic acid and 1, 4-butanediol (dehydrated) and 95 g (0.546 mol) of 2, 4-toluylene diisocyanate at 75 to 85° C. in the course of 1.5 hours. The prepolymer is dissolved in 1060 g of hot tetrahydrofuran and a solution of 53 g (0.13 mol) of an aqueous solution of the sodium salt of N-sulphonatoethylethylenediamine in 100 ml of water is added at 50° C. After 5 minutes, a further 500 g of tetrahydrofuran are added, because of the sharp increase in viscosity. A clear polyurethanepolyurea solution with the following characteristic data is obtained:

| | |
|---|---|
| Solid content: | 35.3% |
| Viscosity (24° C.): | 1000 cp |
| Viscosity (24° C.) of a sample of the solution which has been brought to 30% with tetrahydrofuran: | 400 cp |
| Sulphonate group content: | 14.1 mequivalent/100 g |

Polymer II

The procedure followed is as described for polymer I, but acetone is used as the solvent instead of tetrahydrofuran. 1060 g of acetone and 42.5 g (0.104 mol) of an aqueous solution of the sodium salt of N-sulphonatoethylethylenediamine gives a clear polyurethanepolyurea solution with a solids content of 43.6% and a viscosity of 5700 cp (24° C.). A solution brought to a solids content of 30% has a viscosity of 300 cp (24° C.). The sulphonate group content is 14.1 mequivalent/100 g.

Polymer III

An NCO prepolymer (NCO = 1.68%) is prepared from 400 g (0.178 mol) of a polyester of adipic acid and 1, 4-butanediol (dehydrated) and 47.5 g (0.273 mol) of toluylene diisocyanate (65:35 isomer mixture) as described for polymer I. The prepolymer is dissolved in 980 g of hot acetone and an aqueous solution of 42.5 g (0.104 mol) of the sodium salt of N-sulphonatoethylethylenediamine and 75 ml of water is added at 50° C. A slightly yellow-colored solution of a polyurethane-urea is obtained.

| Solids content: | 30.0% |
| --- | --- |
| Viscosity (23° C.) | 2200 cp |
| Sulphonate group content: | 22.2 mequivalent/100 g |

Polymer IV

An NCO prepolymer (4.11% for NCO) is prepared from 550 g (1.01 mol) of a polyether based on bisphenol A and propylene oxide and 140 g (0.08 mol) of a polyester of phthalic acid, adipic and ethylene glycol (all dehydrated) as well as 145 g (0.239 mol) of a 70% strength solution of the propoxylated adduct of butenediol and sodium bisulphite in toluene and 315 g (1.875 mol) of 1, 6-diisocyanatohexane at 100° C. in the course of 6.5 hours. 77 g (1.283 mol) of urea are added and the mixture is warmed briefly to 135° C. and stirred at 130° C. until no further NCO is detectable in the IR spectrum. 290 ml of water and then 1582 g of acetone are now added, with cooling. A clear slightly yellow-colored solution of a polyurethane -polyurea in acetone is obtained.

| Solids content: | 40% |
| --- | --- |
| Viscosity (23° C.) | 60 cp |
| Sulphonate group content: | 19 mequivalent/100 g |

Polymer V 2200 g (4.0 mol) of a polyether based on bisphenol A and propylene oxide and 115 g (0.053 mol) of monofunctional polyether of n-butanol, propylene oxide and ethylene oxide are dehydrated and 160 g (0.113 mol) of a 70% strength solution of the sodium salt from the description are added to polymer IV in toluene. The mixture is then decomposed with 1096 g (6.30 mol) of toluylene diisocyanate (80:20 isomer mixture, deactivated with 20 mg of hydrogen chloride) at 60° C. The temperature rises to 60° C., in spite of cooling. The mixture is subsequently stirred at 80° C. for 5 hours (NCO=4.95%) and brought to a solids content of 70% with acetone, and reacted with 152 g (1.350 mol) of acetoneketazine.

733 milliliters (ml) of acetone and 95 ml of water are now added to 900 g of this solution and the mixture is stirred overnight at room temperature. A clear polyurethanepolyurea solution is obtained.

| Solids content: | 36.5% |
| --- | --- |
| Viscosity: | 19,000 cp |
| Sulphonate group content: | 7.5 mequivalent/100 g |

A solution brought to a solids content of 30% by dilution with acetone has a viscosity of 3000 cp.

Polymer VI 407.4 g (0.2396 mol) of a hexanediol/neopentyl glycol polyadipate are dehydrated at 120° C. under a water pump vacuum. 77.7 g (0.4625 mol) of 1, 6-diisocyanatohexane are added at 70–80° C. and the mixture is subsequently stirred at 100° C. for 1.5 hours. The prepolymer has an NCO content of 3.5%. After dissolving in acetone to give a 33% strength solution, 75.0 g (0.1924 mol) of Na 2-aminoethyl-$\beta$-aminopropionate (39.5% strength in water) are added at 50° C. and, after 7 minutes, a dispersion is obtained with 1160 ml of completely demineralized water. After the acetone has been distilled off under a water pump vacuum, a very fine-particled dispersion is obtained.

| Data: | |
| --- | --- |
| % Carboxylate group content: | 1.6 = 36.4 mequivalent/100 g |
| % Solids: | 30 |
| pH: | 7.6 |
| Particle size: | 60 m$\mu$ |

Polymer VII 650 g (0.3824 mol) of hexanediol-neopentyl glycol polyadipate and 21 g of a polyoxyethylene-polyoxypropylene (80:20) polyether started on n-butanol and with a molecular weight of 2150 are dehydrated at 120° C. under a water pump vacuum. After cooling to 60° C., 125.6 g (0.7475 mol) of 1, 6-diisocyanatohexane are added and the mixture is warmed to 100° C. and stirred at this temperature for 90 minutes. It is cooled to 60° C. and the reaction production is dissolved in 530 g of acetone. The new 60% strength solution contains 3.1% by weight of NCO.

Water-miscible organic solvents which are suitable for the process of the invention are those which are capable of dissolving both the ionomeric products and the hydrophobic reagents. Examples of such solvents are acetone, tetrahydrofuran, dioxane, isopropanol, methanol, ethanol, methyl ethyl ketone and acetonitrile.

The amounts of hydrophobic reagents used for the process of the invention are in general 2 to 200% by weight of hydrophobic substance per 100% by weight of ionomeric product. Weight ratios of hydrophobic substance to ionomeric product of 1:20 to 1:1 are preferred.

To prepare the dispersions, water is allowed to run into a solution of the water-insoluble hydrophobic reagent and the ionomeric product in a water-miscible low-boiling solvent or solvent/water mixture, with stirring. The solvent is separated off from the dispersion thereby formed by distillation or by other suitable separation processes, such as, for example, dialysis or ultrafiltration.

According to another embodiment, the solution of the water-insoluble hydrophobic reagent in a water-miscible low-boiling solvent can be combined with the solution of a urethane prepolymer which also contains NCO groups, after which the polyaddition is brought to completion in the presence of the hydrophobic substance. This embodiment can be particularly used with advantage if the hydrophobic reagent contains no groups which react with isocyanate.

The process of the invention is outstandingly suitable for incorporating indicators for diagnostic test strips, as the following examples illustrate. EXAMPLE 1

An indicator dispersion can be prepared as follows: 160 g of polymer VI are diluted with 200 ml of acetone. A solution of 48 g of tetraethylbenzidine in 240 ml of acetone is added at room temperature. 420 ml of water are then added dropwise in the course of 20 minutes and the acetone is distilled off in vacuo.

The dispersion prepared in the above manner had solids content of 21% and an average particle size of 92 nm.

EXAMPLE 2

100 g of polymer VI with a solids content of 30% are diluted with 240 ml of acetone and the dilution is warmed to 50° C. A solution of 3 g of 2, 3-naphtho-15-crown-5 and 3 g of 7-decyl-medipine in 150 ml of acetone is then added. After stirring at 50° C. for 30 minutes, 300 ml of water are added dropwise in the course of 30 minutes and the acetone is distilled off on a rotary evaporator.

A fine-particled indicator dispersion with a solids content of 9.8% is thus obtained.

EXAMPLE 3

275 g of the solution of polymer VII are diluted with further acetone to a solids content of 33% and the dilution is warmed to 45° C and stirred with a mixture of
a) 9.62 g of an aqueous solution of the sodium salt of 2-aminoethyl-$\beta$-aminoethanesulphonic acid (50.6% strength in water),
b) 9.78 g of an aqueous solution of the sodium salt of 2-aminoethyl-$\beta$-aminopropionic acid (40.3% strength in water) and
c) 50 g of water.

After 15 minutes, 500 g of a 33% strength acetone solution of tetraethylbenzidine are added, with thorough stirring, and dispersion is then obtained with 730 ml of distilled water in the course of 5-10 minutes. After the acetone has been evaporated off in vacuo, 1130 g of an indicator dispersion with the following data are obtained:

| | |
|---|---|
| Solids content: | 30% |
| PU/TEB ratio: | 1:1 |
| g of TEB in 100 g of dispersion: | 15 |
| Ionogenicity: anionic, $SO_3^-$, + $COO^-$ groups 14.7 mequivalent of $SO_3^-$ + 14.7 mequivalent of $COO^-$/100 g | |
| Particle size: | 90 nanometers (nm) |

EXAMPLE 4

275 g of the solution of polymer VII are diluted with 230 ml of acetone and the dilution is warmed to 50° C. and stirred with a mixture of 50 g of water and 20.4 g of a 50.6% strength aqueous solution of the sodium salt of 2-aminoethyl-$\beta$-aminoethanesulphonic acid. After 10 minutes, a solution of 166 g of tetraethylbenzidine in 335 g of acetone is added, a dispersion is obtained with 765 g of distilled water and the acetone is distilled off in vacuo.

1125 g of a fine-particled aqueous polyurethane dispersion charged with tetraethylbenzidine and with the following data are obtained:

| | |
|---|---|
| Solids content: | 30% |
| pH value: | 8.0 |
| PU/TEB ratio: | 1:1 |
| $SO_3^-$ group content: | 2.5% = 31.3 mequivalent/100 g |

EXAMPLE 5

The procedure followed is analogous to Example 4, but a mixture of 50 g of water and 20.8 g of a 40.3% strength aqueous solution of the sodium salt of 2-aminoethyl-$\beta$-aminopropionic acid is used.

A fine-particled (50 nm) indicator dispersion charged with tetraethylbenzidine is obtained in this manner.

| | |
|---|---|
| Solids content: | 30% |
| pH value: | 8.8 |
| $COO^-$ group content: | 1.4% = 31.8 mequivalent/100 g |

EXAMPLE 6

100 g of a 20% strength gelatin gel of photographic gelatin and 50.0 g of water are melted at 40° C., with stirring. Thereafter, 2.0 g of a 75% strength paste of dodecylbenzenesulphonate (DBS) are added, as well as 50.0 g of an aqueous dispersion of the polymer of Example 1 and 52.705 g of 1.5 molar MES buffer.

Immediately before the casting operation, an aqueous solution of 88.25 g of water, 47.0 g of a glucose oxidase solution (1330 units/ml-Miles), 12.7 g of peroxidase (47 units/mg-Miles) and 1.2 ml of a 4% strength fluoro-surfactant solution is added, so that a total volume of 403.85 ml results.

The casting solution is poured with a wet application of 75 g/m² onto a suitable carrier, such as, for example, polyethylene-laminated photographic base paper with a weight of about 210 g/m², the substrate first having been provided with a thin layer of gelatin to improve adhesion.

In a second operation, a solution of 150.0 ml of a 10% strength solution of a compound which crosslinks with carboxyl groups, such as, for example, SOB 2402, 350.0 ml of water and 10.0 ml of a 4% strength fluoro-surfactant solution is poured, with a wet application of 60 g/m² (corresponding to 1.8 g/m² of hardening agent) onto the dried reaction layer and the system is dried. The hardening agent has a crosslinking effect here on the gelatin molecules, which means that the layer becomes abrasionresistant. SOB 2402 is a carbamoylammonium compound of the formula

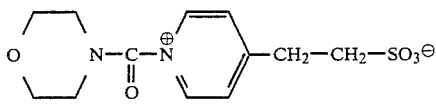

A material which, when provided with glucose solution, generates a green color which, when measured reflectometrically, is a measure of the amount of glucose applied is thus obtained.

EXAMPLE 7

The procedure is as in Example 6, but instead of 100.0 g of 20% strength gelatin gel, only 85.0 g are melted with 93.1 g of water at 40° C., and the ingredients mentioned in Example 4 are added.

In addition, 52.0 of a molten gelatin-containing $TiO_2$ dispersion into which 26.0 g of a 67% strength aqueous barium sulphate paste had first been stirred are added to this casting solution.

The solution is applied, with a wet application of 75 g/m², to a suitable carrier and dried.

In a second operation, a solution of 75.2 g of a 20% strength gelatin gel in 221.8 g of water and 3.0 ml of a 4% strength fluoro-surfactant solution is applied, with a wet application of 40 g/m², to this layer and the layer combination is dried again.

The entire layer combination is finally covered with a layer of a hardener solution of 25.0 ml of a 10% strength solution of a compound which crosslinks with carboxyl groups (SOB 2402), 465.0 g of water and 10 ml of a 4% strength fluoro-surfactant solution with a wet application of 60 g/m² and the system is dried.

The material reacts with glucose solution as a function of the concentration to form a green color, the increase in color being less steep and thus easier to record by instruments.

EXAMPLE 8 (blood sugar test)

For the first operation, as described in Example 7, a casting solution is prepared and poured onto a suitable carrier.

Instead of the second gelatin layer described, however, the dried reaction layer is covered directly with a 60 g/m² layer of a hardener solution of 150.0 ml of a 10% strength solution of a substance with crosslinks with carboxyl groups (SOB 2402) and 10 ml of a 4% strength fluoro-surfactant solution and the system is dried.

The material thus obtained shows the usual reaction with glucose solution with the liquid applied, for example a drop of glucose-containing whole blood, being much easier to wipe off.

EXAMPLE 9

The procedure followed was as in Example 8, but instead of 50.0 g of the polymer of 1, 35.0 g of the polymer of Example 5 were used. The amount of substance which crosslinks with carboxyl groups (SOB 2402) was also reduced from 1.8 g/m² to 0.36 g/m² when covering with a layer of hardener solution.

EXAMPLE 10

A casting solution is prepared as described in Example 9, the polymer of Example 5 being replaced by the polymer of Example 3.

The amount of substance which crosslinks with carboxyl groups (SOB 2402) was also increased to 1.8 g/m².

In contrast to the results of Example 5, the color reaction rapidly comes to an end point, after which the color intensity generated remains stable.

EXAMPLE 11 (blood sugar test)

A casting solution from the following constituents was prepared after the process described in the previous examples:

| gelatin gel (20% strength) | 85.0 g |
| water | 93.546 g |
| DBS (75% strength) | 2.0 g |
| polymer of Example 3 | 35.0 g |
| $TiO_2$ dispersion in gelatin | 39.0 g |
| BES buffer, 1 molar | 41.0 g |
| glucose oxidase solution (1330 units/ml) | 42.3 g |
| peroxidase (47 units/mg) | 12.7 g |
| 4% strength fluoro-surfactant solution | 1.2 ml |

This solution is cast onto a suitable carrier in the customary manner and, after drying, is covered with a layer of a solution of:

| 10% strength SOB 2402 | 150.0 ml |
| water | 340.0 ml |
| 4% strength fluoro-surfactant solution | 10.0 m. | in an amount of 60 g/m² and the system is dried again.

The material thusproduced has an outstanding color graduation in the relation to the concentration of glucose solution applied, the color intensity corresponding to the paticular glucose concentration being reached after about 60–80 seconds.

If glucose-containing whole blood is applied to the layer, the blood can easily be wiped off without trace after an appropriate action time (about 30 seconds).

The material is very stable to storage, even under elevated temperatures, such as, for example, 1 week at 60° C.

EXAMPLE 12 (potassium test)

To prepare the casting solution, 35 g of 20% strength gelatin gel of photographic gelatin are melted at 40° C., and 15 g of TRIS buffer (pH 7–8) are added, with stirring. Thereafter, 50 g of an indicator dispersion as described in Example 2 are added and the solution is cast onto a suitable carrier with a wet application of 70 g/m² in the customary manner.

After drying, a material which shows an excellent and concentration-dependent reactivity when treated with aqueous solutions of potassium salts, a color reaction which is easy to differentiate visually is obtained.

From the foregoing, it will be seen that this invention is well adapted to attain all of the ends and objects hereinbefore set forth, together with other advantages which are obvious and inherent. Obviously, many modifications and variations of the invention as hereinbefore set forth can be made without departing from the spirit and scope thereof and therefore only such limitations should be imposed as are indicated by the appended claims.

What is claimed is:

1. Process for the preparation of a reagent layer for placement upon a substrate, said layer containing hydrophobic reagents wherein an aqueous dispersion of hydrophobic reagents is prepared, said aqueous dispersion being prepared by adding hydrophobic reagents to an ionomeric polymer and dissolving the resulting combination in an organic solvent, thereafter adding water to the resulting mixture and then removing the organic solvent.

2. Process according to claim 1 in which the organic solvent contains up to 50% of water.

3. Process according to claim 1 in which the weight ratio of organic solvent to water is 10:1 to 1:10 after addition of the water.

4. Process according to claim 1 in which the amount of hydrophobic reagents is at least 25% by weight based on the ionomeric polymer.

5. Process according to claim 1 in which the boiling point of the organic solvent is less than 120° C.

6. Process according to claim 1 in which the ionomeric polymer is a polyester, polyamide, polyurea, polycarbonate, polyacetal, polyether or a copolymer thereof.

7. Process according to claim 1 the ionomeric polymer contains 4 to 180 milliequivalents of ionic groups per 100 g of said polymer.

8. Process according to claim 1 in which the ionomeric polymer contains 1 to 20% by weight of ethylene oxide units of the formula $-CH_2-CH_2-O-$ incorporated within a polyethylene chain.

* * * * *